United States Patent
Schramm

(10) Patent No.: US 9,717,691 B2
(45) Date of Patent: Aug. 1, 2017

(54) PHARMACEUTICAL CONTAINING A HORMONE COMBINATION HAVING A CONTRACEPTIVE EFFECT AND AN INSULIN SENSITIZER

(75) Inventor: Georg Schramm, Stolberg (DE)

(73) Assignee: RICHTER GEDEON NYRT., Budapest (HU)

( * ) Notice: Subject to any disclaimer, the term of this patent is extended or adjusted under 35 U.S.C. 154(b) by 305 days.

(21) Appl. No.: 12/793,152

(22) Filed: Jun. 3, 2010

(65) Prior Publication Data
US 2011/0015161 A1 Jan. 20, 2011

Related U.S. Application Data

(63) Continuation of application No. PCT/EP2008/010328, filed on Dec. 5, 2008.

(30) Foreign Application Priority Data

Dec. 5, 2007 (DE) .......................... 10 2007 058 842

(51) Int. Cl.
| A61K 31/565 | (2006.01) |
| A61K 31/57 | (2006.01) |
| A61K 31/4439 | (2006.01) |
| A61K 31/155 | (2006.01) |
| A61K 9/20 | (2006.01) |
| A61K 31/573 | (2006.01) |
| A61K 31/567 | (2006.01) |

(52) U.S. Cl.
CPC .......... *A61K 9/2018* (2013.01); *A61K 31/155* (2013.01); *A61K 31/4439* (2013.01); *A61K 31/565* (2013.01); *A61K 31/567* (2013.01); *A61K 31/57* (2013.01); *A61K 31/573* (2013.01)

(58) Field of Classification Search
None
See application file for complete search history.

(56) References Cited

U.S. PATENT DOCUMENTS

| 2005/0267082 A1* | 12/2005 | Schramm et al. ............ 514/170 |
| 2008/0306150 A1* | 12/2008 | Sharma et al. ............... 514/539 |

FOREIGN PATENT DOCUMENTS

| WO | 02 080971 A | 10/2002 |
| WO | 2005 115350 A | 12/2005 |
| WO | 2007 137797 A | 12/2007 |
| WO | 2008 098318 A | 8/2008 |

OTHER PUBLICATIONS

Glueck et al. (Fertil Steril, 75(1):46-52, 2001, abstract only).*
Glueck et al. (Fertil Steril, 75(1):46-52, 2001).*
Cibula D. et al; "The effect of combination therapy with metformin and combined oral contraceptives (COC) versus COC alone on insulin sensitivity, hyperandrogenaemia, SHBG and lipids in PCOS patients"; Human Reproduction, vol. 20, No. 1, Jan. 2005; pp. 180-184.
Elter Koray et al; "Clinical, endocrine and metabolic effects of metformin added to ethinyl estradiol-cyproterone acetate in non-obese women with polycystic ovarian syndrome: A randomized controlled study"; Human Reproduction (Oxford), vol. 17, No. 7, Jul. 2002, pp. 1729-1737.
Vrbikova J. et al; "Combined oral contraceptives in the treatment of polycystic ovary syndrome"; Human Reproduction Update, Oxford University Press, Oxford, GB vol. 11, No. 3, May 1, 2005, pp. 277-291.
Lemay et al; "Rosiglitazone and ethinyl estradiol/cyproterone acetate as single and combined treatment of overweight women with polycystic ovary syndrome and insulin resistance"; Human Reproduction, Oxford University Press, GB vol. 21, No. 1, Jan. 1, 2006; pp. 121-128.
Tartarin et al.: "Metformin exposure affects human and mouse fetal testicular cells.", Hum Reprod, 2012, Epub, Abstract.
Amador et al.: "Metformin (dimethyl-biguanide) induced DNA damage in mammalian cells.", Benet Mol Biol, 2012, vol. 35(1), pp. 153-158, Abstract.
Ghazeeri et al.: "Pregnancy outcomes and the effect of metformin treatment in women with polycystic ovary syndrome: on overview.", Acta Obstet Gynecol Scand., 2012, vol. 91(6), pp. 658-678, Abstract.

* cited by examiner

*Primary Examiner* — Bong-Sook Baek
(74) *Attorney, Agent, or Firm* — Jason D. Voight

(57) ABSTRACT

The present invention relates to a medicament in the form of daily units, which contain an active ingredient combination consisting of a hormone combination with contraceptive action consisting of at least one oestrogen selected from the group consisting of estradiol and ethinyl estradiol and at least one gestagen selected from the group consisting of chlormadinone acetate, 3-β-OH-chlormadinone acetate, 3-α-OH-chlormadinone acetate, 3-α-acetoxy-chlormadinone acetate and 3-β-acetoxy-chlormadinone acetate, and at least one insulin sensitiser and which are combined to provide a dosage form with daily units which only contain an insulin sensitiser as the sole active ingredient, and to the use of this dosage form for preventing or treating pathological disorders caused by polycystic ovary syndrome (PCOS) and for simultaneous contraception.

15 Claims, No Drawings

PHARMACEUTICAL CONTAINING A HORMONE COMBINATION HAVING A CONTRACEPTIVE EFFECT AND AN INSULIN SENSITIZER

This application is a Continuation of 371 application of PCT/EP2008/010328 filed Dec. 5, 2008, which claims priority to the German application 10 2007 058 842.0 filed Dec. 5, 2007.

The present invention relates to a medicament in the form of daily units, which contain an active ingredient combination consisting of a hormone combination with contraceptive action consisting of at least one oestrogen selected from the group consisting of estradiol and ethinyl estradiol and at least one gestagen selected from the group consisting of chlormadinone acetate, 3-β-OH-chlormadinone acetate, 3-α-OH-chlormadinone acetate, 3-α-acetoxy-chlormadinone acetate and 3-β-acetoxy-chlormadinone acetate, and at least one insulin sensitiser and which are combined to provide a dosage form with daily units which only contain an insulin sensitiser as the sole active ingredient, and to the use of this dosage form for preventing or treating pathological disorders caused by polycystic ovary syndrome (PCOS) and for simultaneous contraception.

With a prevalence of 5 to 10%, polycystic ovary syndrome (PCOS) is one of the commonest diseases of young women. Apart from polycystic ovaries, symptoms of this complaint as it progresses are oligomenorrhoea and amenorrhoea, symptoms of androgenisation, such as hirsutism, acne, alopecia and/or adiposity. Further sequelae of this complaint which are observed include increasing insulin resistance and thus a risk of type II diabetes mellitus, ovulatory dysfunction or even infertility, a greatly increased risk of suffering from endometrial carcinoma, endometrial hyperplasia, ovarian cancer and/or breast cancer and from serious cardiovascular diseases, in particular a greatly increased risk of cardiac infarct.

Women suffering from PCOS and wishing to have children usually cannot do so without pharmaceutical treatment, since irregular ovulation and modified endocrine parameters, such as for example elevated blood sugar values, combine to result in (usually reversible) infertility. PCOS is conventionally treated with the assistance of insulin sensitisers such as for example metformin or glitazones, but these have sometimes considerable side-effects and may, for example, cause lactate acidosis, cardiovascular damage, liver damage or embryo damage. Women being treated for PCOS with insulin sensitisers are therefore conventionally also given contraceptives, since in the event of (unintentional) pregnancy there is an increased risk of damage to the foetus during embryonic development.

The object of the present invention was accordingly to provide a medicament or dosage form which can be used for preventing or treating pathological disorders and long-term sequelae caused by polycystic ovary syndrome, which prevents pregnancy during such therapeutic treatment, and which furthermore, in the event that a child is desired, permits pregnancy with a reduced risk of damage to the foetus during embryonic development after cessation of contraception.

The object is achieved according to the invention by the provision of a medicament which contains an active ingredient combination consisting of a hormone combination with contraceptive action consisting of at least one oestrogen selected from the group consisting of estradiol and ethinyl estradiol and at least one gestagen selected from the group consisting of chlormadinone acetate, 3-β-OH-chlormadinone acetate, 3-α-OH-chlormadinone acetate, 3-α-acetoxy-chlormadinone acetate and 3-β-acetoxy-chlormadinone acetate, and at least one insulin sensitiser, and a dosage form consisting of a specific number of daily units A containing the above-stated active ingredient combination and intended for uninterrupted, daily, oral administration to women and additionally also of 7-3 hormone-free daily units B containing at least one insulin sensitiser as the sole active ingredient component.

The hormone combination and at least one insulin sensitiser are the sole active ingredients of the medicament according to the invention.

For the purposes of the present invention, the term "insulin sensitiser" is taken to mean a substance which counteracts the effects of insulin resistance by lowering the quantity of insulin circulating in the blood. The insulin sensitiser is preferably at least one compound selected from the group consisting of metformin and glitazones and the physiologically acceptable salts thereof, the glitazone preferably being selected from the group consisting of rosiglitazone and pioglitazone. The insulin sensitiser is particularly preferably metformin hydrochloride. The above-stated active ingredients are commercially marketed products.

The hormone combination with a contraceptive action present in the medicament according to the invention preferably contains as the oestrogen component at least one oestrogen selected from the group consisting of estradiol and ethinyl estradiol, natural estradiol being particularly preferred.

Natural estradiol can be produced synthetically. Corresponding syntheses are known.

The hormone combination with a contraceptive action present in the medicament according to the invention preferably contains as the gestagen component at least one gestagen selected from the group consisting of chlormadinone acetate, 3-β-OH-chlormadinone acetate, 3-α-OH-chlormadinone acetate, 3-α-acetoxy-chlormadinone acetate and 3-β-acetoxy-chlormadinone acetate. The gestagen component used according to the invention preferably consists of a single gestagen or of a mixture of gestagens which may be present in any desired mixing ratio in the hormone combination with contraceptive action according to the invention. Antiandrogenic gestagens with a contraceptive action are particularly preferably used.

In a preferred embodiment of the present invention, the gestagen component used according to the invention is one of the following components a) to h)
  a) chlormadinone acetate, or
  b) 3-α-hydroxy-chlormadinone acetate or
  c) 3-β-hydroxy-chlormadinone acetate or
  d) a mixture of a) and b) or of a) and c) or of b) and c) or of a) and b) and c), in each case in any desired mixing ratio or
  e) 3-α-acetoxy-chlormadinone acetate or
  f) 3-β-acetoxy-chlormadinone acetate or
  g) a mixture of e) and f) in any desired mixing ratio or
  h) a mixture of a) and/or b) and/or c) with e) and/or f) in any desired mixing ratio.

In a further preferred embodiment of the present invention, the gestagen component used according to the invention is one of the following components A), B), C) and D)
  A) a mixture according to d), in a mixing ratio of 10 to 90 wt. % chlormadinone acetate a) and 90 to 10 wt. % of b) and/or c), in each case relative to the complete mixture, or B) a mixture of a) and g) in a mixing ratio of 10 to 90 wt. % chlormadinone acetate a) and 90 to 10 wt. % of e) and/or f), in each case relative to the complete mixture, or C) a mixture according to h), in a mixing ratio of 10 to 90 wt. % chlormadinone acetate a) and 90 to 10 wt. % of g), in each case relative to the complete mixture, or D) a mixture of d) and g) in a mixing ratio of 10 to 90 wt. % chlormadinone acetate a) and 90 to 10 wt. % of b), c) and g), in each case relative to the complete mixture.

The medicament according to the invention is preferably provided in the form of a specific number of daily units A, intended for uninterrupted, daily, oral administration to women.

The dosage form according to the invention is obtained by combining the above-stated daily units A preferably with a specific number of daily units B.

The dosage form according to the invention consists of a specific number of daily units A, as described above, intended for uninterrupted, daily, oral administration to women and also additionally of 7-3 hormone-free daily units B containing the above-listed insulin sensitiser as the sole active ingredient intended for uninterrupted, daily, oral administration to women subsequent to administration of the daily units A.

The above-stated daily units A and B preferably assume the form of tablets, preferably film coated tablets.

Each daily unit A preferably contains the gestagen component in each case at least in a contraceptively effective quantity or the oestrogen component in each case at least in a quantity effective for cycle stabilisation. It is here preferred for the quantity of gestagen at least to correspond to the ovulation inhibition dose of the gestagen component used, this preferably being up to 150% above said ovulation inhibition dose. The corresponding ovulation inhibition dose is determined in known manner by the "Hoogland and Skouby" score.

Each daily unit A particularly preferably contains one of the above-listed components a) to h) or A) to D) as the gestagen component. Chlormadinone acetate is particularly preferably used as the sole gestagen component for the daily unit A.

In a preferred embodiment, a daily unit A contains chlormadinone acetate in a quantity of 1 to 10 mg, particularly preferably of 1 to 5 mg, very particularly preferably in each case of 2, 3, 4 or 5 mg, 3α-hydroxy-chlormadinone acetate and/or 3β-hydroxy-chlormadinone acetate in a quantity of 1 to 20 mg, particularly preferably of 1 to 10, very particularly preferably of 1 to 5 mg and estradiol in a quantity of 0.1 to 5 mg, particularly preferably of 0.5 to 3 mg, very particularly preferably of 1 to 2 mg or ethinyl estradiol in a quantity of 0.001 to 50 μg, more preferably of 1 to 50 μg, particularly preferably of 5 to 30 μg and very particularly preferably of 20 to 30 μg, and optionally conventional auxiliary substances.

If the daily units A contain 3α-hydroxy-chlormadinone acetate and/or 3β-hydroxy-chlormadinone acetate or 3-α-acetoxy-chlormadinone acetate and/or 3-β-acetoxy-chlormadinone acetate or a mixture of at least two of the above-stated components, the quantity in each case preferably uniformly amounts to 1 to 20 mg, particularly preferably 1 to 10 mg, the quantity of estradiol or ethinyl estradiol corresponding to the above-stated quantities.

Each daily unit A preferably in each case contains the same quantity of the gestagen component used or the same quantity of the estradiol or ethinyl estradiol used. It is furthermore likewise particularly preferred for each daily unit A to contain the same gestagen component or the same oestrogen component.

Each daily unit preferably contains the same quantity of insulin sensitiser, each daily unit particularly preferably also containing the same insulin sensitiser component. A daily unit A preferably contains 500 to 2000 mg, particularly preferably 1000 to 1500 mg of metformin, preferably as metformin hydrochloride, and/or preferably 2 to 45 mg of at least one glitazone, particularly preferably 5 to 30 mg of pioglitazone or particularly preferably 2 to 8 mg of rosiglitazone.

In a further preferred embodiment of the invention, each daily unit A and B contains the same insulin sensitiser and in each case up to at most the same amount of insulin sensitiser as is present in a daily unit A.

Furthermore, each daily unit B preferably contains up to at most 50 wt. %, particularly preferably up to at most 40 wt. % and no less than 30 wt. % of the quantity of the insulin sensitiser present in a daily unit A, it being particularly preferred for the daily units A and the daily units B to contain the same insulin sensitiser and in each case for each daily unit A or in each case each daily unit B to contain the same quantity of the insulin sensitiser.

This makes it possible, in the event that a woman suffering from PCOS wishes to have a child, to enable a pregnancy with a reduced risk of damage to the foetus during embryonic development after cessation of contraception or therapeutic treatment.

The number of daily units A and B of a dosage form according to the invention may correspond to a natural, monthly, female menstrual cycle. In this case, the dosage form according to the invention preferably comprises at least 21-25 daily units A and 7-3 daily units B to be taken orally daily without interruption. The total number of daily units A and B here preferably amounts to 28, corresponding to a natural, female monthly cycle.

It is, however, also possible for the total number of daily units A, which contain the active ingredient combination according to the invention, to correspond to more than a natural, female monthly cycle, such that a dosage form according to the invention may comprise the daily units A containing the active ingredient combination according to the invention to be taken without interruption for up to 2 years, preferably for up to 1 year, and 7 to 3 hormone-free daily units B containing insulin sensitiser to be taken without interruption immediately subsequently. It is, however, also possible for the dosage form according to the invention to comprise 42 to 52 or 77 to 193 daily units A and 7 to 3 hormone-free daily units containing the insulin sensitiser to be taken without interruption immediately subsequently.

In a preferred embodiment of the present invention, the dosage form according to the invention which comprises the daily units A and B is provided in the form of 28, 56, 84, 112, 140, 168, 196, 224, 252, 280, 308, 336 or 364 daily units for uninterrupted oral, daily administration.

The dosage form according to the invention is suitable for preventing or treating pathological disorders which are caused by polycystic ovary syndrome (PCOS). The medicament according to the invention is particularly preferably suitable for preventing or treating insulin resistance, oligomenorrhoea or amenorrhoea, hyperandrogenaemia, type II diabetes mellitus (T2 DM), obesity, cardiovascular diseases, endometrial hyperplasia, female infertility and/or androgenic disorders, such as hirsutism, acne and/or alopecia, for preventing endometrial carcinoma, mammary carcinoma and/or ovarian cancer, and for simultaneous contraception.

The present invention accordingly also provides the use of an insulin sensitiser for producing a dosage form in the form of the above-described daily units A and B, the daily units A being produced by co-using, in addition to the insulin sensitiser, one of the above-described hormone combinations with a contraceptive action, for preventing or treating pathological disorders which are caused by polycystic ovary syndrome (PCOS). The medicament according to the invention is particularly preferably suitable for preventing or treating insulin resistance, oligomenorrhoea or amenorrhoea, hyperandrogenaemia, type II diabetes mellitus (T2 DM), obesity, cardiovascular diseases, endometrial hyperplasia, female infertility and/or androgenic disorders, such as hirsutism, acne or/and alopecia, for preventing endometrial carcinoma, mammary carcinoma and/or ovarian cancer, and for simultaneous contraception.

The dosage form according to the invention comprising the daily units A and B, as described above, is preferably arranged in a blister pack corresponding to the female menstrual cycle of 28 days, preferably with an indication of the particular daily unit to be taken. More than one blister pack with in each case 28 daily units, each blister pack comprising 21-25 daily units A and 7-3 daily units B, may also be combined into a kit. The kit optionally also includes a calendar or a diary.

EXAMPLES

Example 1

| Composition, daily unit A | |
|---|---|
| | Per tablet |
| Metformin•HCl | 1000 mg |
| Ethinyl estradiol | 0.020 mg |
| Chlormadinone acetate | 3 mg |
| Povidone K30 | 40 mg |
| Microcrystalline cellulose | 200.98 mg |
| Crospovidone | 40 mg |
| Magnesium stearate | 8 mg |
| Highly disperse silicon dioxide | 8 mg |

Ethinyl estradiol (EE) and povidone K30 (polyvinylpyrrolidone, PVP) are dissolved in a sufficient quantity of ethanol. Chlormadinone acetate (particle size 90%<50 µm), microcrystalline cellulose, metformin.HCl and crospovidone are mixed in a mixer/pelletiser (Diosna P25) for 5 mins and then moistened thoroughly and mixed with the aqueous PVP solution. The moist composition is forced through a 3 mm screen and dried in a vacuum drying cabinet. The dried granular product is disagglomerated through a 1.0 mm screen, mixed with magnesium stearate and highly disperse silicon dioxide and pressed into oblong tablets (9×21 mm) with a weight of 1300 mg.

The tablets are coated with a methylhydroxypropylcellulose-based coating (e.g. Opadry YS-1-2184); coating mass 20 mg per tablet.

The daily units B were produced in a similar manner, but without ethinyl estradiol and chlormadinone acetate and with a quantity of 204 mg of microcrystalline cellulose. The daily units B contain 400 mg of metformin.HCl.

28 of these tablets (21 daily units A, 7 daily units B) are packaged in a blister pack marked with days to form a dosage form according to the invention.

Example 2

| Composition, daily unit A | |
|---|---|
| | Per tablet |
| Pioglitazone | 15 mg |
| Estradiol | 1 mg |
| Chlormadinone acetate | 3 mg |
| Povidone K30 | 5 mg |
| Lactose | 54 mg |
| Maize starch | 20 mg |
| Magnesium stearate | 1 mg |
| Highly disperse silicon dioxide | 1 mg |

Estradiol and povidone K30 (polyvinylpyrrolidone, PVP) are dissolved in a sufficient quantity of ethanol. Chlormadinone acetate (particle size 90%<50 µm), lactose, pioglitazone and maize starch are mixed in a mixer/pelletiser (Diosna P25) for 5 mins and then moistened thoroughly and mixed with the ethanolic PVP solution. The moist composition is forced through a 3 mm screen and dried in a vacuum drying cabinet. The dried granular product is disagglomerated through a 0.6 mm screen, mixed with magnesium stearate and highly disperse silicon dioxide and pressed on a tablet press with 7 mm punches into tablets with a weight of 100 mg.

The tablets were coated with a methylhydroxypropylcellulose-based coating (e.g. Opadry YS-1-2184); coating composition 2 mg per tablet The daily units B are produced in a similar manner, but without co-using estradiol and chlormadinone acetate and with a quantity of 65.5 mg of lactose. The daily units B contain 7.5 mg of pioglitazone.

28 of these tablets (21 daily units A, 7 daily units B) are packaged in a blister pack marked with days to form a dosage form according to the invention.

The invention claimed is:

1. A dosage form comprising a medicament containing an active ingredient combination consisting of a hormone combination with contraceptive action, said hormone combination consisting of at least one oestrogen selected from the group consisting of estradiol and ethinyl estradiol and at least one gestagen selected from the group consisting of chlormadinone acetate, 3-β-OH-chlormadinone acetate, 3-α-OH-chlormadinone acetate, 3-α-acetoxy-chlormadinone acetate and 3-β-acetoxy-chlormadinone acetate and at least one insulin sensitiser in the form of a specific number of daily units A intended for uninterrupted, daily, oral administration to women, wherein the dosage form additionally contains 7-3 hormone-free daily units B containing only an insulin sensitiser as active ingredient intended for subsequent, uninterrupted, daily, oral administration to women, and wherein each daily unit A and each daily unit B contain the same insulin sensitizer and each daily unit B contains up to 50 wt. % of the quantity of the insulin sensitiser present in a daily unit A.

2. A dosage form according to claim 1, wherein the insulin sensitiser present in the medicament is selected from the group consisting of metformin, physiologically acceptable salts of metformin and glitazones.

3. A dosage form according to claim 2, wherein the glitazone is a glitazone selected from the group consisting of rosiglitazone, pioglitazone and the physiologically acceptable salts thereof.

4. A dosage form according to claim 1, wherein each daily unit A contains the gestagen component in each case at least in a contraceptively effective quantity or the oestrogen component in each case at least in a quantity effective for cycle stabilisation.

5. A dosage form according to claim 1, wherein each daily unit A contains the same quantity of the gestagen component or the same quantity of the estradiol or of the ethinyl estradiol.

6. A dosage form according to claim 1, wherein each daily unit A contains the same gestagen component.

7. A dosage form according to claim 1, wherein all the daily units A in each case uniformly contain chlormadinone acetate in a quantity of 1 to 10 mg or 3-α-hydroxy-chlormadinone acetate and/or 3-β-hydroxychlormadinone acetate in a quantity of 1 to 20 mg and estradiol in each case uniformly in a quantity of 0.1 to 5 mg or ethinyl estradiol in each case uniformly in a quantity of 0.001 to 50 µg.

8. A dosage form according to claim 1, wherein each daily unit A contains the same quantity of the insulin sensitiser.

9. A dosage form according to claim 1, wherein each daily unit A contains metformin in a quantity of 500 to 2000 mg and/or at least one glitazone in a quantity of 2 to 45 mg.

10. A dosage form according to claim 1, wherein each daily unit B contains no less than 30 wt. % of the quantity of the insulin sensitiser present in a daily unit A.

11. A dosage form according to claim 1, wherein the dosage form comprises at least 21-25 daily units A and 7-3 daily units B.

12. A dosage form according to claim 1, wherein its maximum number of daily units A and B corresponds to uninterrupted administration for 2 years.

13. A method for simultaneously producing a contraceptive effect, and preventing or treating pathological disorders caused by polycystic ovary syndrome (PCOS), said method comprising administering to a patient in need thereof a dosage form according to claim 1.

14. A dosage form according to claim 1, wherein each daily unit B contains up to 40 wt. % and no less than 30 wt. % of the quantity of the insulin sensitiser present in a daily unit A.

15. A dosage form according to claim 14, wherein each daily unit A contains the same quantity of the insulin sensitiser and each daily unit B contains the same quantity of the insulin sensitiser.

* * * * *